United States Patent [19]  
Kaplan et al.

[11] 4,416,874  
[45] Nov. 22, 1983

[54] INJECTABLE COMPOSITIONS OF BBM-928A

[75] Inventors: Murray A. Kaplan, Syracuse; Edward C. Shinal, Manlius, both of N.Y.

[73] Assignee: Bristol-Myers Company, New York, N.Y.

[21] Appl. No.: 354,998

[22] Filed: Mar. 5, 1982

[51] Int. Cl.³ ............................................. A61K 37/02
[52] U.S. Cl. .................................................. 424/177
[58] Field of Search .................. 424/177; 260/112.5 R

[56] References Cited

U.S. PATENT DOCUMENTS 4,360,458  11/1982  Koshiyama et al. ................ 424/177

FOREIGN PATENT DOCUMENTS 2050384  3/1980  United Kingdom .

OTHER PUBLICATIONS

Del et al., J.A.C.S., 97, 2497–2502 (1975).
Osol, Remington's Pharmaceutical Sciences, 16th Ed., p. 1265, Mack Publishing Co., Easton, Pennsylvania (1980).
Windhalz, The Merck Index, 9th Ed. Merck and Co. Inc., p. 1115 (1976).
Physicians Desk Reference, 37th Edition, 1983, Parenteral Dilantin.

Primary Examiner—Delbert R. Phillips
Assistant Examiner—F. T. Moezie
Attorney, Agent, or Firm—Robert E. Carnahan

[57] ABSTRACT

BBM-928A solutions suitable for parenteral use in animal experiments and having concentrations in the range of 1 mg/ml to 5 mg/ml are described.

8 Claims, No Drawings

INJECTABLE COMPOSITIONS OF BBM-928A

DESCRIPTION OF THE PRIOR ART

Reference is made to the Konishi et al. paper published in Peptide Chemistry 1980, Protein Research Foundation Osaka, Japan 1981, pp. 119–124 and entitled "Structure Determination of a New Antitumor Antibiotic, BBM-928". BBM-928A is a decadepsipeptide in the diacetate form which may be converted to the monoacetate (BBM-928B) or to the desacetoxy form (BBM-928C). BBM-928A is thus the diacetate of BBM-928C. BBM-928A is a potent antitumor antibiotic while BBM-928C is almost devoid of antitumor activity. These substances are subject to mild alkaline hydrolysis (0.1 N sodium hydroxide to pH 13 25° C. 3 hours) to yield a linear peptide fragment which is devoid of antitumor activity.

The only solvents in which BBM-928A is readily soluble are chloroform and methylene chloride (Ohkuma et al. "BBM-928. A New Antitumor Antibiotic Complex I. Production, Isolation, Characterization and Antitumor Activity" The Journal of Antibiotics, vol. 33, No. 10 pp. 1087–1097 October 1980) which solvents are not acceptable for injection into or ingestion by mammals including man. Is thus evident that due to the hydrolytic sensitivity and insolubility of BBM-928A that a formidable pharmaceutical formulation problem is presented for the intravenous use thereof.

The BBM-928 antibiotic complex has also been described in West German Patent Application No. P30125656 published Oct. 23, 1980.

BBM-928A, BBM-928B, BBM-928C have the following structural formulas:

The disodium salt of BBM-928A has been prepared by dissolving BBM-928A in aqueous sodium hydroxide at pH 10.5, washing with chloroform, and lyophilizing the aqueous solution. Its solubility in water is 0.5 mg/ml. In the dry state disodium BBM-928A gradually decomposes to BBM-928B and BBM-928C at higher temperatures. The following Table exemplifies this:

| Temperature | Residual Disodium BBM-928A After Storage for Various Periods | | | |
|---|---|---|---|---|
| | 0 Days | 7 Days | 14 Days | 21 Days |
| 5° C. | 100 | 98.0 | 97.2 | 96.3 |
| 37° C. | 100 | 91.6 | 90.6 | 88.8 |
| 45° C. | 100 | 88.2 | 87.5 | 84.9 |

Solutions of disodium BBM-928A are decomposed much more quickly. This is illustrated in the following tabulation which presents for illustrative purposes only measurements on solutions on disodium BBM-928A in 50% aqueous methanol at a starting concentration of 5 mg/ml. which, of course, is not an injectable composition due to the use of methanol.

| Temperature | Disodium BBM-928A Remaining in Solution After Storage for Various Periods | | | | | |
|---|---|---|---|---|---|---|
| | 0 hours | 2 hours | 4 hours | 6 hours | 20 hours | 28 hours |
| 5° C. | 100 | 96 | 96 | 95 | 90 | 84 |
| 25° C. | 100 | 95 | 93 | 89 | 83 | 70 |

BBM-928A can be administered by injection to animals when dissolved in aqueous sodium carbonate at a concentration of 0.5 mg of BBM-928A per milliliter of solution containing 1 micromole of sodium carbonate (pH 10.4) which is then diluted tenfold with saline.

It is an object of the present invention to provide injectable solutions of BBM-928A suitable for parenteral administration. For convenience in animal experiments it is desirable to administer doses of up to 10 mg of BBM-928A in volumes as small as 2 ml. While more dilute solutions are sometimes applicable, the availability of the injectable dosage forms having lower volumes made possible by the present invention greatly facilitates experimental studies.

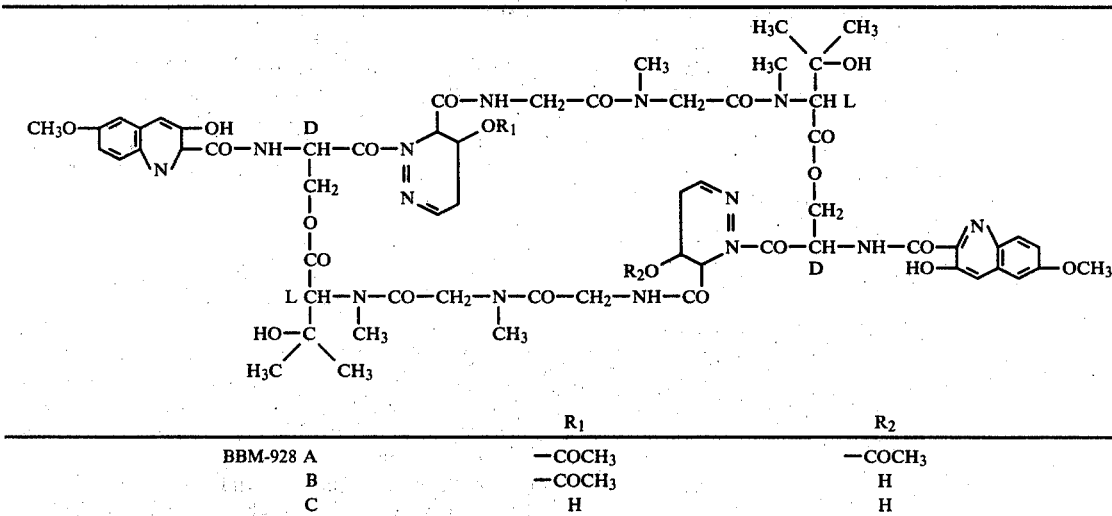

|  | $R_1$ | $R_2$ |
|---|---|---|
| BBM-928 A | —COCH$_3$ | —COCH$_3$ |
| B | —COCH$_3$ | H |
| C | H | H |

DETAILED DESCRIPTION OF THE INVENTION

BBM-928A was found to be virtually insoluble in 22 commonly employed pharmaceutical vehicles including various poloxamer polyols, benzyl alcohol, ethanol, peanut oil, cottonseed oil, soybean oil, propylene glycol, polyethylene glycol 400, 45% urea solution, 4% povidone solution, 40% nicotinamide solution, 40% dextrose solution, ethyl oleate, 50% lactamide solution, 25% sodium levulinate solution and levulinic acid. Limited solubility in the following solvents was observed.

Ethyl lactate, about 1 mg/ml with slight haze; can be diluted with one half volume of water or one volume of polyethylene glycol 400 or propylene glycol; immiscible with fixed oils.

Ethyl levulinate, 0.5 mg/ml by allowing the BBM-928A to stand in contact with the solvent overnight, may be diluted with one half volume of water or one volume of polyethylene glycol 400 or propylene glycol; immiscible with soybean oil but not with peanut oil.

Lactic acid U.S.P., 1 mg/ml; immiscible with fixed oils and produces cloudiness when contacted with water; may be diluted with an equal volume of polyethylene glycol 400 or propylene glycol.

Aqueous L-arginine 10%, 1 mg/ml to afford a yellow solution with a slight haze; immiscible with fixed oils may be diluted with an equal volume of polyethylene glycol 400 or propylene glycol; haziness develops on dilution with an equal volume of water; similar results using 1-arginine 1% as solvent.

It has been found that injectable solutions of BBM-928A may be prepared having concentrations up to ten times as great as those referred to above with respect to disodium BBM-928A if the pH of the solution is adjusted to within the range of pH 11.0 to 11.5 with a water soluble base which is pharmaceutically acceptable for intravenous injection purposes. Sodium hydroxide, trisodium phosphate, sodium carbonate and the sodium salts of weak acids having pKa values in excess of pKa 6.3 may be used. Suitable sodium salts include trisodium orthophosphate, sodium carbonate and the sodium salts of various organic acids such as glycine, aspartic acid, cysteine, phthalic acid, succinic acid, and tyrosine. Suitable organic bases which may be used to prepare the intravenous solutions of the present invention are those which are non-toxic, pharmacologically inactive and acceptable for intravenous use. These include such bases having a pKa value in excess of pKa 11 examples of which are pyrrolidine, triethylamine, piperidine, glucosamine, and N-methylglucamine.

The preferred composition of the present invention employs trisodium orthophosphate as the base for solubilization of BBM-928A. Solutions having concentrations of BBM-928A of from 1 to 5 mg per milliliter are readily prepared when 0.65 parts by weight of trisodium orthophosphate per part by weight of BBM-928A are employed. Such solutions have a pH within the range of 11.0 to 11.5. If an amount of the base is employed which is insufficient to provide a pH value of pH 11.0 the desired level of solubilization of the BBM-928A is not achieved. At pH values in excess of 11.5 decomposition through hydrolysis of the BBM-928A becomes so extensive as to result in loss of utility of the solutions. It has been found that intravenous solutions of BBM-928A solubilized by trisodium phosphate in the range of pH 11.0 to 11.5 are sufficiently stable for the use during a period of up to 4 hours following preparation. Such solutions should not be kept for longer periods but should be prepared extemporaneously prior to use. Conventional aseptic techniques conforming to the criteria of both good laboratory practices and good manufacturing practices should be employed in preparing the compositions of the present invention.

A preferred composition is a dry mixture of BBM-928A and trisodium phosphate in the proportion of one part by weight of BBM-928A and 0.65 parts by weight of trisodium orthophosphate. This mixture may be subdivided into dosage units which are distributed to vials containing 16.5 mg. of the mixture and which are aseptically sealed under conditions of 50% relative humidity or less. The contents of a single vial are then dissolved in from 2 to 10 ml. of water to provide an injectable solution having a BBM-928A concentration of from 1 to 5 mg/ml. Such solutions may be injected as such or further diluted with an intravenous drip solution such as saline or dextrose.

Alternatively the BBM-928A may be subdivided into dosage unit vials containing 10 mg. of the pure, sterile substance each, and a trisodium phosphate solution prepared and packaged separately in amounts of from 2 to 10 milliliters per unit each containing 6.5 mg. of $Na_3PO_4$ for use in dissolving the 10 mg. dosage units of BBM-928A.

DESCRIPTION OF SPECIFIC EMBODIMENTS

Formulation A

Sterile BBM-928A and sterile anhydrous sodium orthophosphate in the following quantities are intimately admixed in a sterile work area maintained at 50% relative humidity using a suitable blending device:
sterile BBM-928A (60–100 mesh) 10.0 g.
sterile anhydrous $Na_3PO_4$ 6.5 g.
The resulting bulk powder is then filled into glass vials at the rate of 16.5 mg. per vial (10 mg. BBM-928A), and the vials sealed by a proper closure to maintain the anhydrous sterile condition. The batch is sufficient for 1000 vials. Each vial is constituted for intravenous injection with the desired quantity of sterile water for injection in an amount of 2 ml. or more per vial (conc. up to 5 mg/ml. and preferably from 1 to 5 mg/ml. of BBM-928A). Stability tests and analysis by high performance liquid chromatography have confirmed the suitability for use within 4 hours after dissolving.

Alternatively the BBM-928A may be packaged separately in a sealed glass vial as in Formulation A and a solution of sodium phosphate may be used for constitution of it for intravenous injection. This is illustrated below:

Formulation B

Sterile BBM-928A is filled into sterile glass vials at the rate of 10 mg. per vial in a sterile work area maintained at 50% relative humidity. A sterile solution of sodium phosphate is prepared having a concentration of sodium phosphate of 0.65 mg. per ml. and 10 ml. portions are filled into separate vials. All vials are sealed under aseptic conditions. Just prior to use the contents of a vial containing the sodium phosphate solution are mixed with the contents of a vial containing the BBM-928A to provide a solution which is identical with that provided on constitution of Formulation A with 10 ml. of water.

It has been found that some lots of BBM-928A fail to dissolve in aqueous solution with water soluble bases suitable for pharmaceutical injection purposes at pH 11.0 to 11.5 according to the present invention. The reason for this is not known, but such material can be converted into a suitable form for the preparation of the water soluble compositions of the present invention by crystallization from methylene chloride. The crystallization is carried out by dissolving the BBM-928A in methylene chloride and then evaporating the solvent from the solution. The crystals form during the evaporation process. The process is not believed to result in purification of the material since the entire volume of solvent is evaporated and the BBM-928A is simply converted into a new more soluble form. The following procedure is suitable:

BBM-928A CRYSTALS DERIVED FROM METHYLENE CHLORIDE EVAPORATION (1) Dissolve one gram of BBM-928A in 50 ml of spectral grade methylene chloride.

(2) Pass the solution under vacuum through a fine glass filter. Wash the filter with 15 ml of methylene chloride. Add the wash to the filtrate. Some crystals may be present in the cold methylene chloride composite solution. If required add methylene chloride to obtain 50-60 ml solution. Warming the solution to room temperature (22° C.) will solubilize any crystals present.

(3) Place approximately one quarter of the BBM-928A methylene chloride solution in a 50 ml round evaporation flask. Remove the solvent on a Rotovapor at 40° C. waterbath and at aspirator vacuum. Repeat with one quarter volume until all the methylene chloride is evaporated.

(4) Maintain aspirator vacuum at 40° C. on the flask of crystals for one hour.

(5) Dry the flask of crystals at 40°–50° C.: high vacuum for 5 hours.

(6) If required, the crystals may be scraped from the side of the flask and placed in a separate container.

What is claimed is:

1. A pharmaceutical composition suitable for intravenous injection comprising a sterile aqueous solution containing from 1 mg. to 5 mg. of BBM 928A per milliliter, and sufficient of a pharmaceutically acceptable water soluble base to solubilize said BBM 928A and confer a pH value of from pH 11.0 to 11.5 upon said solution wherein said base is selected from the group consisting of sodium hydroxide, trisodium phosphate, sodium carbonate, pyrrolidine, triethylamine, piperidine, glucosamine, N-methylglucamine, and the sodium salt of an organic acid selected from the group consisting of glycine, aspartic acid, cysteine, phthalic acid, succinic acid, and tyrosine.

2. The intravenous solution of claim 1 wherein said base is sodium hydroxide.

3. The intravenous solution of claim 1 wherein said base is trisodium orthophosphate.

4. The intravenous solution of claim 1 wherein said base is the sodium salt of glycine, aspartic acid, cysteine, phthalic acid, succinic acid, or tyrosine.

5. The intravenous solution of claim 1 wherein said base is pyrrolidine, triethylamine, or piperidine.

6. A dry composition suitable for constitution with sterile water for injection comprising one part by weight of BBM 928A and 0.65 parts by weight of trisodium orthophosphate.

7. The composition of claim 6 in dosage unit form providing 10 mg. of BBM 928A for constitution with 2 milliliters of water.

8. A pharmaceutical composition suitable for intravenous injection comprising a sterile aqueous solution containing one part by weight of BBM 928A and 0.65 parts by weight of trisodium orthophosphate and sufficient water to provide a BBM 928A concentration of from 1 to 5 mg. per milliliter.

* * * * *